United States Patent [19]
Stjernschantz et al.

[11] Patent Number: 6,030,999
[45] Date of Patent: *Feb. 29, 2000

[54] PROSTAGLANDIN DERIVATIVES FOR THE TREATMENT OF GLAUCOMA OR OCULAR HYPERTENSION

[75] Inventors: Johan Wilhelm Stjernschantz; Bahram Resul, both of Uppsala, Sweden

[73] Assignee: Pharmacia & Upjohn Aktiebolag, Stockholm, Sweden

[*] Notice: This patent is subject to a terminal disclaimer.

[21] Appl. No.: 09/307,814

[22] Filed: May 10, 1999

Related U.S. Application Data

[60] Continuation of application No. 08/461,341, Jun. 5, 1995, which is a division of application No. 07/986,943, Dec. 8, 1992, Pat. No. 5,422,368, which is a continuation of application No. 07/469,442, Apr. 10, 1990, abandoned.

[51] Int. Cl.⁷ ............................................. A61K 31/557
[52] U.S. Cl. ............................................................ 514/530
[58] Field of Search ............................................. 514/530

[56] References Cited

U.S. PATENT DOCUMENTS

| | | |
|---|---|---|
| 3,956,284 | 5/1976 | Hess et al. . |
| 3,962,312 | 6/1976 | Hayashi et al. . |
| 3,987,087 | 10/1976 | Bundy . |
| 4,001,300 | 1/1977 | Axen . |
| 4,011,262 | 3/1977 | Hess et al. . |
| 4,061,865 | 12/1977 | Hatashi et al. . |
| 4,115,586 | 9/1978 | Miller, Jr. . |
| 4,116,988 | 9/1978 | Nelson . |
| 4,117,119 | 9/1978 | Kurono et al. . |
| 4,128,713 | 12/1978 | Schneider . |
| 4,131,738 | 12/1978 | Smith . |
| 4,599,353 | 7/1986 | Bito . |
| 4,820,728 | 4/1989 | Collins et al. . |
| 4,824,857 | 4/1989 | Goh et al. . |
| 4,883,819 | 11/1989 | Bito . |
| 5,001,153 | 3/1991 | Ueno et al. . |
| 5,057,621 | 10/1991 | Cooper et al. . |
| 5,151,444 | 9/1992 | Ueno et al. . |
| 5,166,178 | 11/1992 | Ueno . |
| 5,194,429 | 3/1993 | Ueno . |
| 5,422,368 | 6/1995 | Stjernschantz ........................ 514/530 |
| 5,849,791 | 12/1998 | Stjernschantz ........................ 514/530 |

FOREIGN PATENT DOCUMENTS

| | | |
|---|---|---|
| 573018 | 2/1986 | Australia . |
| 600168 | 8/1990 | Australia . |
| 986926 | 4/1976 | Canada . |
| 170258 | 2/1986 | European Pat. Off. . |
| 242580 | 10/1987 | European Pat. Off. . |
| 253094 | 1/1988 | European Pat. Off. . |
| 238135 | 8/1988 | European Pat. Off. . |
| 281239 | 9/1988 | European Pat. Off. . |
| 289349 | 11/1988 | European Pat. Off. . |
| 308135 | 3/1989 | European Pat. Off. . |
| 364417 | 4/1990 | European Pat. Off. . |
| 366279 | 5/1990 | European Pat. Off. . |
| 455264 A2 | 11/1991 | European Pat. Off. . |
| 2234709 | 2/1973 | Germany . |
| 1324737 | 7/1973 | United Kingdom . |
| WO90/02553 | 3/1990 | WIPO . |

OTHER PUBLICATIONS

Bill A (1975) "Blood Circulation and fluid dynamics in the eye". *Physiol. Rew.* 55: 383–417.

Bito LZ, Draga, A, Blanco DJ, Camras CB (1983) "Long Term Maintenance of Reduced intraocular Pressure by Daily or Twice Daily Topical Application of Prostaglandins to Cat or Rhesus Monk,ey Eyes" *Invest. Ophthalmol. Vis. Sci.* 24: 312–319.

Bito, Baroody and Miranda (1987): Eicosanoids as a new class of ocular Hypotensive agents. The apparent therapeutic advantage of derived Prostaglandins of the A and B type as compared with primary prostaglandins of the E, F and D types, Experimental Eye Research, 44:825.

Bito LZ, Camras CB, Gumm GG and Resul B (1989). "The Ocular Hypotensive Effects and Side Effects of Prostaglandins on the Eyes of Experimental Animals" *Progress in Clinical and Biological Research* 312 Ed. LZ Bito and Johan Stjernschantz, A.R. Liss, Inc., New York.

Burke et l., Prostaglandin $F_{2\alpha}$ Effects on Rabbit IOP Negatively Correlate with Classical $PGF_{2\alpha}$–Receptor Stimulation Presented at ARVO annual meeting in Florida May 1–6, 1988.

Bundy, Chem Abst. 90:168141d, 1979.

Camras CB, Bito LZ (1981). Reduction of intraocular pressure in normal and glaucomatous primate (*Aotus trivirgatus*) eyes by topically applied prostaglandin $F_{2\alpha}$. *Curr Eye Res.* 1:205–209.

Camras, CB, Podos, SM, Rosenthal JS, Lee PY, Severin CH (1987a). Multiple dosing of prostaglandin $F_{2a}$ or epinephrine on cynomolgus monkey eyes. I. Aqueous humor dynamics. *Invest. Ophthalmol Vis Sci* 28:463–469.

Camras C B, Bito L Z and Eakins K E (1977): "Reduction of intraocular pressure by prostaglandins applied to the eyes of concious rabbits", Invest Ophthalmol Vis. Sci, 16:1125.

Camras CB, Bhuyan KC, Podos, SM, Bhuyan DK Master RWP (1987b) "Multiple Dosing of Prostaglandin $F_{2\alpha}$ or epinephrine on cynomologus mokey eyes. II. Slitlamp biomicroscopy, aqueous humor analysis, and fluorescein angiography." *Invest. Ophthalmol. Vis. Sci.* 28: 921–926.

Camras, CB, Siebold ED, Lustgarten JS, Serle JB, Frisch SC, Podos SM, Bito LZ (1988) "Reduction of IOP by prostaglandin $F_{2\alpha}$–1–isopropyl ester topically applied in glaucoma patients", *Ophthalmology* 95(Suppl.) 129 [This article is referrenced in the specfication, and was raised as prior art in an opposition to Australian patent application 625096, which is related to the instant application. However, we have been unable to locate a copy of this article. ].

(List continued on next page.)

*Primary Examiner*—Robert Gerstl
*Attorney, Agent, or Firm*—Kenyon & Kenyon

[57] ABSTRACT

The invention relates to ophthalmological compositions for topical treatment of glaucoma or ocular hypertension comprising an effective intraocular pressure reducing amount of a prostaglandin derivative of PGA, PGB, PGD, PGE or PGF, in which the omega chain contains a ring structure, in an ophthalmologically compatible carrier. The invention further relates to the preparation of said compositions and their use for treatment of glaucoma or ocular hypertension.

1 Claim, No Drawings

OTHER PUBLICATIONS

Crawford K, Kaufman PL and True Gabel, BA (1987), "Pilocarpine antagonizes $PGF_{2\alpha}$–induced ocular hypotension: Evidence for enhancement of uveoscleral outflow of $PGF_{2\alpha}$." *Invest. Ophthalmol. Vis. Sci.* (Suppl) ARVO Abstracts 11.

Crawford, K and Kaufman, P.L., (1987) "Pilocarpine Antagonizes Prostaglandin $F_{2\alpha}$–Induced Ocular Hypotension in Monkeys" Arch. Ophthamology 105 1112.

Flach AJ, Elisason JA (1988). Topical prostaglandin $E_2$ effects on normal intraocular pressure. *J. Ocu. Pharmacol.* 4:13–18.

Gabelt, B. and Kaufman, P.L., (1989)"Prostaglandin $F_{2\alpha}$ Increases Uvelscleral Outflow in the Cynomologus Monkey", Exp. Eye Res. 49 389–402.

Giuffré G. (1985). "The effects of prostaglandin $F_{2\alpha}$ in the human eye." *Graefes Arch Clin. Exp. Ophthalmol.* 222:139–141.

Goldberg I, Kolker A.E., Kass M.A. and Becker B (1980) "Dipivefrin: current concepts", Australia J. Ophthalmol., 8:147.

Granstrom, E., (1975) "Metabolism of 17–Phenyl–18,19, 20–Trinor–Prostaglandin $F_{2\alpha}$ in the Cynomolgus Monkey and the Human Female", *Prostaglandins* 9:19–45.

Kass, M.A., Posos, S.M., Moses, R.A., and Becker B. (1972): Prostaglandin E1 and aqueous humor dynamics, Invest. Ophthalmol. 11:1022.

Kass M.A., Mandell Al, Goldberg I, Paine J.M. and Becker B (1979) "Dipivefrin and epinephrine treatment of elevated intraocular pressure: A comparative study", Arch Ophthalmol. 97:1865.

Kaufman PL (1986). "Effects on intracamerally infused prostaglandins on outflow facility in cynomolgus monkey eyes with intact or retrodisplaced ciliary muscle." *Exp. Eye Res.* 43:819–827.

Kerstetter J R, Brubaker, R F, Wilson S E and Kullerstrand B S (1987): "Prostaglandin F2 alpha 1–isopropyl ester effects on aqueous humor dynamics in human subjects", Invest Ophthalmol Vis Sci Suppl, 28:266.

Kerstetter J R, Brubaker, R F, Wilson S E and Kullerstrand L (1988) "Prostaglandin $F2_\alpha$–1– Isopropylester Lowers Intracolor Pressure Without Decreasing Aqueous Humor Flow". Am. J. Ophthalmology 105:30–34.

Kirk–Othmar "Encyclopedia of Chemical Technology", 3d Ed. Supplement vol. 711–752 (1984).

Lee, P–Y, Shae H, XZu L, Qu C–K (1988). The effect of prostaglandin $F_{2\alpha}$ on intraocular pressure in normotensive human subjects. *Invest. Ophthalmol. Vis. Sci.* 29:1474–1477.

Miller, "Biological Activities of 17–phenyl–18,19, 20–trinorprostaglandins", *Prostaglandins* 9 9–18 (1975).

Nilsson, SFE, Stjernschantz J and Bill A (1987) $PGF_{2\alpha}$ increase uveoscleral outflow. *Invest. Ophthalmol Vis. Sci. Suppl.* 284.

Ritch, Shields and Krupin (1989): "The Glaucomas", C V Mosby, p 561.

Starr, M.S. (1971) Further studies on the effect of prostaglandin on intraocular pressure in the rabit, Exp. Eye, Res. 11:170.

Villumsen J, Alm A, Soderstrom M, (1989) "Prostaglandin F2α–isopropylester Eye Drops: Effect on Intraocular Pressure in Open Angle Glaucoma". Brit. J. Ophthalmology 73, 975–79.

Villumsen J. Alm A (1989) "Prostaglandin $F_{2\alpha}$ isopropylester eye drops. Effects in normal human eyes." *Br. J. Ophthalmol.* 73:419–426.

Villumsen J and Alm A (1987): "The effect of prostaglandin F2α eye drops in open angle glaucoma", Invest Opthalmol. Vis. Sci. 28:378.

Wang R–F, Cmamras, C.B., Lee P–Y, Podos S.M. and Bito LZ (1987) The ocular hypotensive effects of Prostaglandins $F2_\alpha$ isopropyl ester and A2 in glautomatous monkeys Invest Ophthalmol Vis Sci ARVO Supl. 28:266.

Yankee, Chem Abst. 88:62048, 1978.

Woodward et al., Prostaglandin $F_{2\alpha}$ Effects on IOP Negatively Correlate with Classical $PFG_{2\alpha}$–Receptor Stimuluation Presented in Eightly International Congress of Eye Research in San Francisco Sep. 4–8, 1988.

Woodward et al. (1989) "Prostaglandin $F_{2\alpha}$ Effects on Intraocular Pressure Negatively Correlate with FP–Receptor Stimulation" *Invest. Ophthal.* 30 (8) 1838–1842.

Supplement to Investigative Ophthalmology and Visual Science 22 39 (1982), L.Z. Bito, A. Draga, J. Blanco, and C.B. Camras, "Maintenance of Reduced Intraocular Pressure (IOP) for several months by topical application of prostaglandin (PG) $E_1$ to Eyes of Trained Cats".

Abstracts 12 and 13 on p. 325 of ARVO Annual Meeting Abstract Issue 1988 of Annual Meeting: Sarasota, Florida May 1–6, 1988.

Abstracts 31, 33 and 35 on p. 35 of Abstracts 8th International Congress of Eye Research, San Francisco, Sep. 4–8, 1988.

Journal of Medicinal Chemistry, vol. 23, 1980, pp. 525–535.

Annual Reports in Medicinal Chemistry, vol. 11, 1976, pp. 80–88.

Zajacz: IRCS Medical Science: Clinical Medicine; Clinical Pharmacology and Therapeutics: Drug Metabolism and Toxicology; The Eye: Reproduction, Obstetrics and Gynecology, vol. 4, 1976, p. 316.

Miranda and Bito: The Ocular Effects of Prostaglandins and Other Eicosanoids, 1989, pp. 171–195.

ASPET abstract: Pharmacologist, vol. 29, 1987, p. 139, 33/178.

Investigative Ophthalmology & Visual Science, vol. 31, 1990, pp. 2560–2567.

The Ocular Effects of Prostaglandins and Other Eicosanoids, 1989, p. 179.

Journal of Ocular Pharmacology, vol. 9, 1991, p. 189.

The Association for Research in Vision and Ophthalmology, Annual Spring Meeting, Sarasota, FL, May 1–6, 1988: Investigative Ophthalmology & Visual Science, vol. 29, supplement p. 325, abstracts 12 and 13.

Prostaglandins and Medicine, 3, 1979, pp. 33–37.

Bito: Experimental Eye Research, vol. 39, 1984, pp. 807–829.

Archives of Ophthalmology, vol. 105, 1987, pp. 1036–1039.

Archives of Ophthalmology, vol. 106, 1988, pp. 449–450.

The Ocular Effects of Prostaglandins and Other Eicosanoids, 1989, pp. 349–368.

Investigative Ophthalmology & Visual Science, vol. 25, 1984, 1087–93.

Prostaglandins, vol. 12, 1976, pp. 493–500.

Prostaglandins, vol. 10, 1975, pp. 5–18.

Arch. Ophthalmol.—vol. 105, Feb. 1987, 249–252.

Exp. Eye Res. (1984) 38, 181–194.

Exp. Eye Res. (1987) 44, 825–837.

ARVO abstracts 266, 5.

PROSTAGLANDIN DERIVATIVES FOR THE TREATMENT OF GLAUCOMA OR OCULAR HYPERTENSION

This application is a continuation application of application Ser. No. 08/461,341, filed on Jun. 5, 1995, which is a division of application Ser. No. 07/986,943, filed on Dec. 8, 1992, now U.S. Pat. No. 5,422,368, which is a continuation of application Ser. No. 07/469,442, filed on Apr. 10, 1990, abandoned.

The invention is concerned with the use of prostaglandin derivatives of PGA, PGB, PGD, PGE and PGF, in which the omega chain has been modified with the common feature of containing a ring structure, for the treatment of glaucoma or ocular hypertension. The invention relates also to ophthalmic compositions, containing an active amount of these prostaglandin derivatives, and the manufacture of such compositions.

Glaucoma is an eye disorder characterized by increased intraocular pressure, excavation of the optic nerve head and gradual loss of the visual field. An abnormally high intraocular pressure is commonly known to be detrimental to the eye, and there are clear indications that, in glaucoma patients, this probably is the most important factor causing degenerative changes in the retina. The pathophysiological mechanism of open angle glaucoma is, however, still unknown. Unless treated successfully glaucoma will lead to blindness sooner or later, its course towards that stage is typically slow with progressive loss of the vision.

The intraocular pressure, IOP (abbr. of intraocular pressure) can be defined as according to the formula:

$$IOP = P_e + F \times R \qquad (1)$$

where $P_e$ is the episcleral venous pressure, generally regarded as being around 9 mm Hg, F the flow of aqueous humor, and R the resistance to outflow of aqueous humor through the trabecular meshwork and adjacent tissue into Schlemm's canal.

Besides passing through Schlemm's, canal aqueous humor might also pass through the ciliary muscle into the suprachoroidal space and finally leave the eye through sclera. This uveoscleral route has been described for instance by Bill (1975). The pressure gradient in this case is insignificant compared to the gradient over the interior wall of Schlemm's canal and adjacent tissue in the former case. The flow limiting step along the uveoscleral route is assumed to be the flow from the anterior chamber into the suprachoroidal space.

A more complete formula is given by:

$$IOP = P_e + (F_t - F_u) \times R \qquad (2)$$

where $P_e$ and R are defined as above, $F_t$ is the total outflow of aqueous humor and $F_u$ is the fraction passing via the uveoscleral route.

IOP in human beings is normally in the range of 12–22 mm Hg. At higher values, for instance over 22 mm Hg, there is a risk that the eye may be affected. In one particular form of glaucoma, low tension glaucoma, damage may occur at intraocular pressure levels otherwise regarded as physiologically normal. The reason for this could be that the eye in these individuals is unusually sensitive to pressure. The opposite situation is also known, that some individuals may exhibit an abnormally high intraocular pressure without any manifest defects in the visual field or optic nerve head. Such conditions are usually referred to as ocular hypertension.

Glaucoma treatments can be given by means of drugs, laser or surgery. In drug treatment, the purpose is to lower either the flow (F) or the resistance (R) which, according to formula (1) above, will result in a reduced IOP; alternatively to increase the flow via the uveoscleral route which according to formula (2) also gives a reduced pressure. Cholinergic agonists, for instance pilocarpine, reduce the intraocular pressure mainly by increasing the outflow through Schlemm's canal.

Prostaglandins, which recently have met an increasing interest as IOP-lowering substances may be active in that they will cause an increase in the uveoscleral outflow (Crawford et al, 1987, and Nilsson et al, 1987). They do not appear, however to have any effect on the formation of aqueous humor or on the conventional outflow through Schlemm's canal (Crawford et al, 1987).

The use of prostaglandins and their derivatives is described for instance in U.S. Pat. No. 4,599,353 and EP 87103714.9, and by Bito L Z et al (1983), Camras C B et al (1981, 1987a, 1987b, 1988), Giuffrè G (1985), Kaufman P L (1986), Kersetter J R et al (1988), Lee P-Y et al (1988) and Villumsen J et al (1989).

With respect to the practical usefulness of some of the previously described prostaglandins and derivatives, as suitable drugs for treating glaucoma or ocular hypertension, a limiting factor is their property of causing superficial irritation and vasodilation in the conjunctiva. It is probable, moreover, that prostaglandins have an irritant effect on the sensory nerves of the cornea. Thus local side effects will arise in the eye already when the amounts of prostaglandin administered are quite small—that is, already when the doses are lower than those that would be desirable for achieving maximum pressure reduction. It has thus been found, for instance, that for this reason it is clinically impossible to use $PGF_{2\alpha}$-1-isopropyl ester in the amount that would give maximum pressure reduction. Prostaglandins, being naturally occurring autacoids, are very potent pharmacologically and affect both sensory nerves and smooth muscle of the blood vessels. Since the effects caused by administrations of $PGF_{2\alpha}$ and its esters to the eye, comprise in addition to pressure reduction also irritation and hyperemia (increased blood flow), the doses currently practicable in clinical tests are necessarily very low. The irritation experienced when $PGF_{2\alpha}$ or its esters are applied, consists mainly in a feeling of grittiness or of having a foreign body in one's eye, this being usually accompanied by increased lacrimation.

We have now found that a solution to the problems discussed above is the use of certain derivatives of prostaglandins A, B, D, E and F, in which the omega chain has been modified with the common feature of containing a ring structure, for the treatment of glaucoma or ocular hypertension.

The prostaglandin derivatives have the general structure

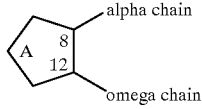

wherein A represents the alicyclic ring $C_8$–$C_{12}$ and the bonds between the ring and the side chains represent the various isomers. In PGA, PGB, PGD, PGE and PGF A has the formula

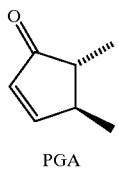
PGA

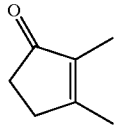
PGB

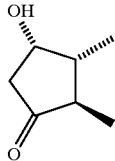
PGD

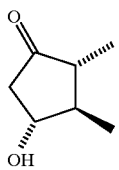
PGE

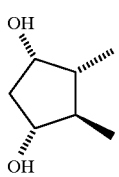
PGF

The invention is based on the use of derivatives characterized by their omega chain and various modifications of the alpha chain is therefore possible still using the inventive concept. The alpha chain could typically be the naturally occuring alpha chain, which is esterified to the structure

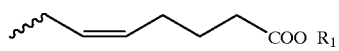

in which $R_1$ is an alkyl group, preferably with 1–10 carbon, especially 1–6 atoms, for instance metyl, ethyl, propyl, isopropyl, butyl, isobutyl, neopentyl or benzyl or a derivative giving the final substance equivalent properties as a glaucoma agent. The chain could preferably be a $C_6$–$C_{10}$ chain which might be saturated or unsaturated having one or more double bonds, and allenes, or a triple bond and the chain might contain one or more substituents such as alkyl groups, alicyclic rings, or aromatic rings with or without hetero atoms.

The omega chain is defined by the following formula:

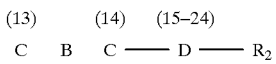

wherein
C is a carbon atom (the number is indicated within parenthesis)
B is a single bond, a double bond or a triple bond
D is a chain with 1–10, preferably 2–8, and especially 2–5, and particularly 3 carbon atoms, optionally interrupted by preferably not more than two hetero atoms (O, S, or N), the substituent on each carbon atom being H, alkyl groups, preferably lower alkyl groups within 1–5 carbon atoms, a carbonyl group, or a hydroxyl group, whereby the substituent on $C_{15}$ preferably being a carbonyl group, or (R)—OH or (S)—OH; each chain D containing preferably not more than three hydroxyl groups or not more than three carbonyl groups,
$R_2$ is a ring structure such as a phenyl group which is unsubstituted or has at least one substituent selected from $C_1$–$C_5$ alkyl groups, $C_1$–$C_4$ alkoxy groups, trifluoromethyl groups, $C_1$–$C_3$ aliphatic acylamino groups, nitro groups, halogen atoms, and phenyl group; or an aromatic heterocyclic group having 5–6 ring atoms, like thiazol, imidazole, pyrrolidine, thiophene and oxazole; or a cycloalkane or a cycloalkene with 3–7 carbon atoms in the ring, optionally substituted with lower alkyl groups with 1–5 carbon atoms.

Some examples on derivatives which were evaluated are the following (for structure information see Table I):
(1) 16-phenyl-17,18,19,20-tetranor-$PGF_{2\alpha}$-isopropylester
(2) 17-phenyl-18,19,20-trinor-$PGF_{2\alpha}$-isopropylester
(3) 15-dehydro-17-phenyl-18,19,20-trinor-$PGF_{2\alpha}$-isopropylester
(4) 16-phenoxy-17,18,19,2-tetranor-$PGF_{2\alpha}$-isopropylester
(5) 17-phenyl-18,19,20-trinor-$PGE_2$-isopropylester
(6) 13,14-dihydro-17-phenyl-18,19,20-trinor-$PGA_2$-isopropylester
(7) 15-(R)-17-phenyl-18,19,20-trinor-$PGF_{2\alpha}$-isopropylester
(8) 16-[4-(methoxy)-phenyl]-17,18,19,20-tetranor-$PGF_{2\alpha}$-isopropylester
(9) 13,14-dihydro-17-phenyl-18,19,20-trinor-$PGF_{2\alpha}$-isopropylester
(10) 18-phenyl-19,20-dinor-$PGF_{2\alpha}$-isopropylester
(20) 19-phenyl-20-nor-$PGF_{2\alpha}$-isopropylester The most preferred derivatives at present are those in which the omega chain of the prostaglandin has the 18,19,20-trinor form, and especially the 17-phenyl analogs, such as the 15-(R)-, 15-dehydro and 13,14-dihydro-17-phenyl-18,19,20-trinor forms. Such derivatives are represented by (3), (6), (7) and (9) in the formulas given in Table I.

In the formula given above the most preferred structure at present is accordingly obtained when the prostaglandin is a derivative of PGA, PGD, PGE or PGF, especially of $PGA_2$, $PGD_2$, $PGE_2$ and $PGF_2a$
B is a single bond or a double bond
D is a carbon chain with 2–5, especially 3 atoms; $C_{15}$ having a carbonyl or (S)—OH substituent and $C_{16}$–$C_{19}$ having lower alkyl substituents, or preferably H
$R_2$ is a phenyl ring optionally having substituents selected among alkyl and alkoxy groups.

The invention thus relates to the use of certain derivatives of PGA, PGB, PGD, PGE and PGF for the treatment of glaucoma or ocular hypertension. Among these derivatives defined above it has been found that some are irritating or otherwise not optimal, and in certain cases not even useful due to adverse effects and these are excluded in that the group of prostaglandin derivatives defined above is limited to therapeutically effective and physiologically acceptable derivatives. So is for instance (1) 16-phenyl-17,18,19,20-tetranor-PGF$_{2\alpha}$-isopropyl ester irritating while this can be eliminated by substituting the phenyl ring with a methoxy group giving formula (8) which represents a therapeutically more useful compound, The method for treating glaucoma or ocular hypertension consists in contacting an effective intraocular pressure reducing amount of a composition, as aforesaid, with the eye in order to reduce the eye pessure and to maintain said pressure on a reduced level. The composition contains 0.1–30 μg, especially 1–10 μg, per application of the active substance i.e. a therapeutically active and physiologically acceptable derivative from the group defined above; the treatment may advantageously be carried out in that one drop of the composition, corresponding to about 30 μl is administered about 1 to 2 times per day to the patient's eye. This therapy is applicable both to human beings and to animals.

The invention further relates to the use of therapeutically active and physiologically acceptable prostaglandin derivatives from the group defined above for the preparation of an ophthalmological composition for the treatment of glaucoma or ocular hypertension.

The prostaglandin derivative is mixed with an ophthalmologically compatible vehicle known per se. The vehicle which may be employed for preparing compositions of this invention comprises aqueous solutions as e.g. physiological salines, oil solutions or ointments. The vehicle furthermore may contain ophthalmologically compatible preservatives such as e.g. benzalkonium chloride, surfactants like e.g. polysorbate 80, liposomes or polymers, for example methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to ophthalmological compositions for topical treatment of glaucoma or ocular hypertension which comprise an effective intra ocular pressure reducing amount of a prostaglandin derivative as defined above and an ophthalmologically compatible carrier, the effective amount comprising a dose of about 0.1–30 μ in about 10–50 μ of the composition.

In the experiments carried out in this investigation the active compound, in an amount, varying with potency of the drug, from 30 μg to 300 μg/ml was dissolved in a sterilized aqueous solution (saline 0.9%) containing 0.5% polysorbate-80 as solubilizing agent.

The invention is illustrated by means of the following non-limitative examples.
Synthesis of prostaglandin derivatives

EXAMPLE 1

Preparation of 16-phenyl-17,18,19,20-tetranor PGF$_{2\alpha}$-isopropyl ester (1).

A 50 ml round bottom flask equipped with a magnetic stirring bar was charged with 17.5 mg (0.04 mmol) 16-phenyl-17,18,19,20-tetranor PGF$_2$a (Cayman Chemical), 5 ml CH$_2$C$_{12}$,30.2 mg (0.23 mmol) diisopropylethylamine. This solution was stirred at −10° C. and 13.5 mg (0.07 mmol) of isopropyltriflate (freshly prepared) was added. This solution was allowed to stand at −10° C. for 15 min and was then slowly warmed to room temperature. When the esterification was complete according to TLC (usually after 3–4 h at room temperature) the solvent was removed in vacuo. The residue was diluted with 20 ml ethylacetate, washed with 2×10 ml 5% sodium hydrogencarbonate and 2×10 ml 3% citric acid. The organic layer was dried over unhydrous sodium sulfate. The solvent was removed in vacuo and the residue was purified by column chromatography on silica gel-60 using ethyl acetate:aceton 2:1 as eluent. The title compound was obtained as a colourless oily substance (71% yield).

Nuclear Magnetic Resonance spectrum (CDCl$_3$)—ppm: δ

| 1.2 | (6H d) | 3.3 | (1H q) |
| 2.85 | (2H d) | 5.0 | (1H m) |
| 3.85 | (1H m) | 5.3–5.7 | (4H m) |
| 4.15 | (1H t) | 7.15–7.35 | (5H m) |

EXAMPLE 2

Preparation of 17-phenyl-18,19,20-trinor PGF$_{2\alpha}$-isopropyl ester (2).

A 50 ml round bottom flask equipped with a magnetic stirring bar was charged whith 20 mg (0.05 mmol) 17-phenyl-18,19,20-trinor PGF$_{2\alpha}$ (Cayman Chemicals), 6 ml acetone, 39.2 mg (0.25 mmol) DBU and 42.5 mg (0.25 mmol) isopropyl iodide. The solution was allowed to stand at room temperature for 24 h, the solvent was removed in vacuo and the residue was diluted with 30 ml of ethyl acetate, washed twice with 10 ml 5% sodiumhydrogen carbonate and 10 ml 3% citric acid. The solvent was removed in vacuo, and the crude product was chromatographed on silica gel-60 using ethyl acetate:acetone 2:1 as eluent. The title compound (2) was obtained as an oily substance (65% yield).

Nuclear Magnetic Resonance spectrum (CDCl$_3$)—ppm: δ

| 1.2 | (6 m) | 4.9 | (1H m) |
| 3.9 | (1H m) | 5.4–5.6 | (4H m) |
| 4.1 | (1H t) | 7.1–7.3 | (5H m) |
| 4.2 | (1H m) | | |

EXAMPLE 3

Preparation of 15-dehydro-17-phenyl-18,19,20-trinor PGF$_{2\alpha}$-isopropyl ester (3)

20.9 mg (0.092 mmol) DDQ was added to a solution of 10 mg (0.023 mmol) 17-phenyl-18,19,20 trinor PGF$_{2\alpha}$-isopropyl ester (2) in 8 ml dioxane. The reaction mixture immediately turned brown, the reaction mixture was stirred at room temperature for 24 h. The precipitate formed was filtered, washed with 10 ml ethyl acetate, the filtrate was diluted with 10 ml ethylacetate washed with 2×10 ml water, 2×10 ml NaOH IM and 20 ml brine. The organic layer was dried on unhydrous sodium sulfate and the solvent was removed in vacuo, the residue was purified by column chromatography on silica gel using ethyl acetate:ether 1:1 as eluent. The title compound (3) was obtained as a colourless oily substance (76% yield).

Nuclear Magnetic Resonance spectrum (CDCl$_3$),—ppm: δ

| 1.2 | (6H d) | 5.4 | (2H m) |
|---|---|---|---|
| 4.0 | (1H m) | 6.2 | (1H d) |
| 4.2 | (1H m) | 6.7 | (1H q) |
| 5.0 | (1H m) | 7.15–7.35 | (5H m) |

EXAMPLE 4

Preparation of 16-phenoxy-17,18,19,20 -tetranor PGF$_{2\alpha}$-isopropyl ester(4).

Following a procedure similar to that described in example 2 using 20 mg (0.051 mmol) 16-phenoxy-17,18, 19,20 -tetranor PGF$_{2\alpha}$ (Cayman Chemicals). The title compound (4) was an oily substance (53.2% yield).
Nuclear Magnetic Resonance spectrum (CDCl$_3$)—ppm: δ

| 1.2 | (6H d) | 5.4 | (2H m) |
|---|---|---|---|
| 3.9 | (3H m) | 5.7 | (2H m) |
| 4.2 | (1H m) | 6.9 | (3H m) |
| 4.5 | (1H m) | 7.3 | (2H m) |
| 5.0 | (1H m) | | |

EXAMPLE 5

Preparation of 17-phenyl-18,19,20-trinor PGE$_2$-isopropyl ester (5).

Following a procedure similar to that described in example 2 using 10 mg (0.026 mmol) 17-phenyl-18,19,20-trinor PGE$_2$ (Cayman Chemicals). The crude product was purified by column chromatography on silica gel-60 using ether as eluent. The title compound (5) was an oily substance (38.9% yield).
Nuclear Magnetic Resonance spectrum (CDCl$_3$)—ppm: δ

| 1.2 | (6H d) | 5.3 | (2H m) |
|---|---|---|---|
| 3.9–4.1 | (2H m) | 5.6 | (2H m) |
| 4.9 | (1H m) | 7.2 | (5H m) |

EXAMPLE 6

Preparation of 13,14-dihydro-17-phenyl-18,19,20-trinor PGA$_{2\alpha}$-isopropyl ester (6).

Following a procedure similar to that described in example 2 using 10 mg (0.026 mmol) 13,14-dihydro-17-phenyl PGA$_2$ (Cayman Chemicals). The crude product was chromatographed on silica gel-60 using ether as eluent.
Nuclear Magnetic Resonance spectrum (CDCl$_3$)—ppm: δ

| 1.2 | (6H d) | 5.4 | (2H m) |
|---|---|---|---|
| 4.35 | (1H m) | 7.3 | (5H m) |
| 5.0 | (1H m) | | |

EXAMPLE 7

Preparation of 15-(R)-17-phenyl-18,19,20-trinor PGF$_{2\alpha}$-isopropyl ester (7). (Table II)

7.1 Preparation of 1-(S)-2-oxa-3-oxo-6-(R)-(3-oxo-5-phenyl-1-trans-pentenyl)-7-(R)-(4-phenylbenzoyloxy)-cis-bicyclo [3,3,0] octane (13).

18 g (0.05 mol) alcohol (11), 32 g (0.15 mol) DCC, 39.1 g (0.5 mol) DMSO (newly distilled from CaH$_2$) and 30 ml DME were charged to a 200 ml flask under nitrogen. Orthophosphoric acid was added in one portion, and an exothermic reaction occured. The reaction mixture was stirred mechanically at room temperature for 2h, and the resultant precipitate was filtered and washed with DME. The filtrate (12) can be used directly for Emmon condensation reaction.

To a suspension of 1.2 g (0.04 mol) NaH (80% washed with n-pentane to remove mineral oil) in 100 ml DME under nitrogen was added dropwise 12.3 g (0.048) dimethyl-2-oxo-4-phenyl-butyl-phosphonate in 30 ml DME. The mixture was stirred mechanically for 1h at room temperature, then cooled to −10° C. and a solution of the crude aldehyde (12) was added in dropwise. After 15 min at 0° C. and 1 h at room temperature the reaction mixture was neutralized with glacial acetic acid, the solvent was removed under vaccum, and to the residue was added 100 ml ethyl acetate, washed with 50 ml water and 50 ml brine. The organic layer was dried over unhydrous sodium sulfate. The solvent was removed in vacuo and the resulting white precipitate filtered and washed with cold ether. The title compound (13) was obtained as a crystalline substance mp 134.5–135.5 (53% yield).

7.2 Preparation of 1-(S)-2-oxa-3oxo-6-(R)-[3-(R,S)-hydroxy-4-phenyl-1-trans-pentenyl]-7-(R)-(4-phenylbenzoyloxy) cis-bicyclo [3,3,0]octane (14).

10 g (0.021 mol) enone (13) and 3.1 g (0,008 mol) cerous-chloride heptahydrate in 50 ml methanol and 20 ml CH$_2$Cl$_2$ were charged to a 200 ml round bottom flask equipped with a magnetic stirring bar and was cooled to −78° C. under nitrogen. Sodium borohydride was added in small portions, after 30 min the reaction mixture was quenched by addition of saturated NH$_4$Cl, and extracted with 2×50 ml ethyl acetate. The extracts were dried and concentrated to leave a colourless oil (98% yield).

7.3 Preparation of 1-(S)-2-oxa-3-oxo-6-(R)-[3-(R,S)-hydroxy-4-phenyl-1-trans-pentenyl]-7-(R)-hydroxy-cis-bicyclo-[3,3,0] octane (15).

To a solution of 9.8 g (0.02 mol) ketal (14) in 100 ml absolute methanol was added 1.7 (0.012 mol) potassium carbonate. The mixture was stirred with a magnetic bar, at room temperature after 3 h. The mixture was neutralized with 40 ml HCl 1 M, and extracted with 2×50 ml ethyl acetate. The extracts were then dried on unhydrous sodium sulfate and concentrated. The crude product was chromatographed on silica gel using ethyl acetate: acetone as eluent. The title compound (15) was obtained as an oily substance (85% yield).

7.4 Preparation of 1-(S)-2-oxa-3-hydroxy-6-(R)-[3-(R,S)-hydroxy-4-phenyl-1-trans-pentenyl]-7-(R)-hydroxy-cis-bicyclo[3,3,0] (16).

To a solution of 3 g (0.011 mol) lactone (15) in 60 ml unhydrous THF, stirred magnetically and cooled to −78° C., 4.5 g (0.0315 mol) DIBAL-H in toluene was added dropwise. After 2 h the reaction mixture was quenched by addition of 75 ml methanol. The mixture was filtered, the filtrate was concentrated in vacuo and the residue was chromatographed on silica gel-60 using ethyl acetate:acetone 1:1 as eluent. The title compound (16) was obtained as a semisolid substance (78% yield).

7.5 Preparation of 15-(R,S)-17-phenyl-18,19,20-trinor PGF$_{2\alpha}$(17).

2.5 g (25 mmol) sodium methyl sulfinylmethide in DMSO (freshly prepared from sodium anhydride and DMSO) was added dropwise to a solution of 5.6 g (12.6 mmol)

4-caboxybutyl triphenyl-phosphonium bromide in 12 ml DMSO. To the resultant red solution of the ylide was added dropwise a solution of the 1.2 g (4.2 mmol) hemiacetal (16) in 13 ml DMSO, and the mixture was stirred for 1 h. The reaction mixture was diluted with 10 g ice and 10 ml water and extracted with 2×50 ml ethyl acetate, whereafter the aqueous layer was cooled, acidified with HCl 1 M and extracted with ethyl acetate, and then the organic layer was dried and concentrated. The resulting crude product was a colourless substance. The purity of the title compound (17) was estimated by TLC on silica gel using ethyl acetate:acetone:acetic acid 1:1:0.2 v/v/v as eluent.

7.6 Preparation of 15-(R)-17-phenyl-18,19,20-trinor $PGF_{2\alpha}$-isopropyl ester (7).

The crude product (17) was esterified following a procedure similar to that described in example 2 the product was purified by column chromatography on silica gel-60 using ethyl acetate as eluent and the resulting mixture of $C_{15}$ epimeric alcohol were separated.

The title compound (7) was obtained as a colourless oily substance (46% yield).

Nuclear Magnetic Resonance spectrum ($CDCl_3$),—ppm: δ

| 1.2  | (6H m) | 5.4 | (2H m) |
|------|--------|-----|--------|
| 3.9  | (1H m) | 5.6 | (2H m) |
| 4.15 | (2H m) | 7.2 | (5H m) |
| 4.95 | (1H m) |     |        |

EXAMPLE 8

Preparation of 16-[4-(methoxy)phenyl]-17,18,19,20-tetranor $PGF_{2\alpha}$-isopropyl ester (8).

Following a procedure similar to that described in example 7 with modified step 7-2, the aldehyde 12 described in step 7-2 was reacted with dimethyl-2-oxo-3-[4-(methoxy) phenyl]-propylphosphonate and was purified by column chromatography on silica gel-60 using ethyl acetate:toluene 1:1 as eluent. A colourless oily substance was obtained (57% yield).

The title compound 16-[4-(methoxy)phenyl]-17,18,19, 20-tetranor $PGF_{2\alpha}$-isopropyl ester (8) was obtained as an oily substance, and purified by column chromatography on silica gel-60 using ethyl acetate as eluent (46% yield).

Nuclear Magnetic Resonance spectrum ($CDCl_3$)—ppm: δ

| 1.2  | (6H d) | 5.0 | (1H m) |
|------|--------|-----|--------|
| 2.8  | (2H d) | 5.4 | (2H m) |
| 3.75 | (3H S) | 5.6 | (2H m) |
| 3.9  | (1H m) | 6.8 | (2H d) |
| 4.15 | (1H m) | 7.2 | (2H d) |
| 4.3  | (1H m) |     |        |

EXAMPLE 9

Preparation of 13,14-dihydro-17-phenyl-18,19,20-trinor $PGF_{2\alpha}$-isopropyl ester (9).

Following a procedure similar to that described in example 7, with minor modification, 5 g (0.018 mol) enone (13) in 100 ml THF was reduced using 2.03 g 10% pd/c under hydrogen atmosphere. After completion of the reaction (as determined by TLC on silica gel using ethylacetate-:toluene 1:1 as eluent) the mixture was filtered on celite. The filtrate was concentrated in vacuo and an oily substance was obtained (86% yield).

The final product 13,14-dihydro-17-phenyl-18,19,20-trinor $PGF_{2\alpha}$-isopropyl ester containing a mixture of $C_{15}$ epimeric alcohols were separated by preparative liquid chromatography using 40% $CH_3CN$ in water v/v as eluent.

Nuclear Magnetic Renonance spectrum ($CDCl_3$)—ppm: δ

| 1.2  | (6H d) | 5.0 | (1H m) |
|------|--------|-----|--------|
| 3.6  | (1H m) | 5.4 | (2H m) |
| 3.9  | (1H m) | 7.2 | (5H m) |
| 4.15 | (1H m) |     |        |

EXAMPLE 10

Preparation of 18-phenyl-19,20-trinor $PGF_{2\alpha}$-isopropyl ester (10).

Following a procedure similar to that described in example (7) with modified step 7-2. The aldehyde (12) described in 7-2 was reacted with dimethyl-2-oxo-5-phenyl pentyl phosphonate gave a crystalline substance trans-enone lactone (67% yield).

The final product 18-phenyl-19,20-dinor $PGF_{2\alpha}$-isopropyl ester (10) was purified by column chromatography on silica gel-60 using ethyl acetate as eluent gave a colourless oil (41% yield).

| 1.2  | (6H d) | 5.0 | (1H m) |
|------|--------|-----|--------|
| 3.95 | (1H m) | 5.4 | (2H m) |
| 4.10 | (1H m) | 5.6 | (2H q) |
| 4.20 | (1H m) | 7.2 | (5H m) |

EXAMPLE 11

Preparation of 19-phenyl-20-nor-$PGF_{2\alpha}$-isopropyl ester (20).

Following a procedure similar to that described in example (7) with modified step (7-2).

The aldehyde (12) described in (7-2) was reacted with dimethyl-2-oxo-6-phenyl-hexylphosphonate gave a colourless oil trans-enone lactone (56% yield).

The final product 19-phenyl-20-nor-$PGF_{2\alpha}$-isopropyl ester (20) was a colourless oil, and was purified by column chromatography on silica gel-60 using ethyl acetate as eluent (30% yield).

Nuclear Magnetic Resonance spectrum ($CDCl_3$)—ppm: δ

| 1.2 | (6H d) | 5.0 | (1H m) |
|-----|--------|-----|--------|
| 2.6 | (2H t) | 5.4 | (2H m) |
| 3.9 | (1H m) | 5.5 | (2H t) |
| 4.1 | (1H m) | 7.2 | (5H m) |
| 4.2 | (1H m) |     |        |

Studies of eye pressure lowering effect and adverse reactions

The intraocular pressure (IOP) was determined in animals TM with a pneumatonometer (Digilab Modular One™, Bio Rad), specially calibrated for the eye of the particular species. The cornea was anaesthetized with 1–2 drops of oxibuprocain before each IOP measurement. In healthy human volunteers IOP was measured with applanation tonometry or with an air puff tonometer (Keeler pulsair). For applanation tonometry either a pneumatonometer (Digilab) or Goldmann's applanation tonometer mounted on a slit lamp microscope was used. The cornea was anaesthetized with oxibuprocain before each measurement with applanation tonometry. No local anaesthesia was employed before measurement with the pulsair tonometer.

The ocular discomfort after application of the test substances was evaluated in cats. The behaviour of cats after topical application of the test drug was followed and ocular discomfort was graded on a scale from 0 to 3, 0 indicating complete absence of any signs of discomfort, and 3 indicating maximal irritation as obvious from complete lid closure.

Conjunctival hyperemia after topical application of the test substances was evaluated in rabbits. The conjunctiva at the insertion of the superior rectus muscle of the eye was inspected or photographed with regular intervals and the degree of hyperemia was later evaluated from the color photographs in a blind manner. Conjunctival hyperemia was evaluated on a scale from 0 to 4, 0 indicating complete absence of any hyperemia, and 4 indicating marked hyperemia with conjunctival chemosis.

For determination of the effects on the intraocular pressure, primarily monkeys (cynomolgus) were employed. The reason for this is that the monkey eye is highly reminiscent of the human eye and therefor, generally, drug effects are readily extrapolated to the human eye. However, the disadvantage of using the monkey eye as a model is that the conjunctiva in this species is pigmented making it impossible to evaluate conjunctival hyperemia and furthermore, the monkey eye is relatively insensitive to irritation. Therefore, the cat eye, being very sensitive to prostaglandins was used for evaluating ocular discomfort and the rabbit eye with pronounced tendency to hyperemic reactions was used for evaluating conjunctival and episcleral hyperemia.

It is evident from Table III that modification of the omega chain of the prostaglandin skeleton introduced new and unexpected features to the prostaglandins with respect to ocular irritation (discomfort). Particularly 17-phenyl, 18,19, 20-trinor-$PGF_{2\alpha}$-IE and analogs were unique in exhibiting a complete loss of ocular irritation with retained IOP lowering effect in monkeys. Whereas the 17-phenyl,18,19,20-trinor-$PGF_{2\alpha}$ derivatives were extremely well tolerated, 16-phenyl-17,18,19,20-tetranor-$PGF_{2\alpha}$-IE caused clear ocular discomfort although to a lesser degree than $PGF_{2\alpha}$-IE or 15-propionate-$PGE_2$-IE (Table III). However, substituting a hydrogen atom in the phenyl ring with a methoxy group having electron donating properties rendered the molecule practically free of ocular irritating effect, Table III. It is also evident from Table III that 18-phenyl-19,20,-dinor-$PGF_{2\alpha}$IE, 19-phenyl-20-nor-$PGF_{2\alpha}$-IE as well as 17-phenyl-18,19,20-trinor-$PGE_2$-IE and 13,14-dihydro-17-phenyl-18,19,20-trinor-$PGA_2$-IE, had no or very little irritating effect in the eye of cats. This indicates that the invention not only is valid for 16-, and 17-tetra- and trinor analogs of $PGF_{2\alpha}$ but for a range of omega chain modified and ring substituted analogs of $PGF_{2\alpha}$(as exemplified with 16-phenyl-17,18,19,20-tetranor-$PGF_{2\alpha}$-IE to 19-phenyl-20-nor-$PGF_{2\alpha}$-IE), and more importantly even for different members of the prostaglandin family such as $PGE_2$ and $PGA_2$ modified in an analogous way (Table III). Thus, modifying the omega chain and substituting a carbon atom in the chain with a ring structure introduces completely new, unexpected and advantageous qualities to naturally occuring prostaglandins in that the irritating effect in the conjunctiva and cornea is abolished. In the case of 16-phenyl-17,18,19, 20-tetranor-$PGF_{2\alpha}$-IE exhibiting some irritating effect substituting a hydrogen atom in the ring structure with e.g. a methoxy group attenuates or abolishes the irritating effect.

In addition to the lack of ocular discomfort the omega chain modified analogs also exhibited an advantage over naturally occuring prostalgandins in that they caused considerably less conjunctival hyperemia as studied in the rabbit eye (Table IV). Particularly, 15-dehydro-17-phenyl-18,19, 20-trinor-$PGF_{2\alpha}$-IE,13,14-dihydro-17-phenyl-18,19,20-trinor-$PGF_{2\alpha}$-IE, and 13,14-dihydro-17-phenyl-18,19,20-trinor $PGA_{2\alpha}$-IE were advantageous in this respect. Also 18-phenyl-19,20-dinor-$PGF_{2\alpha}$-IE and 19-phenyl-20-nor-$PGF_{2\alpha}$-IE induced very little conjunctival hyperemia (Table IV).

The intraocular pressure lowering effect of omega chain modified and ring-substituted prostaglandin analogs is demonstrated in Table V. It can be seen that particularly 16-phenyl-tetranor and 17-phenyl-trinor prostaglandin analogs significantly reduced IOP in animal eyes (Table V). In all but two series of experiments cynomolgus monkeys were used. It is of particular interest to note that 17-phenyl-18, 19,20-trinor $PGF_{2\alpha}$-derivatives exhibiting no ocular irritation and only modest conjunctival/episcleral hyperemia significantly lowered IOP in primates. It should furthermore be observed that both 16-phenyl-17,18,19,20-tetranor-$PGF_\alpha$-IE, 18-phenyl-19,20-dinor-$PGF_{2\alpha}$-IE and 19-phenyl-20-nor-$PGF_\alpha$-IE reduced the intraocular pressure, thus, modification of the omega chain and substituting a carbon atom in the chain with a ring structure do not render the molecule inactive with respect to the effect on the intraocular pressure.

Furthermore, it should be observed that substituting a hydrogen on the ring structure of 16-phenyl,17,18,19,20-tetranor-$PGF_{2\alpha}$-IE with a methoxy group eliminated much of the ocular irritating effect preserving most of the intraocular pressure lowering effect. Thus, omega chain modified and ring substituted prostaglandin analogs reduce IOP effectively in animals. It is further demonstrated in Table V that 16-phenoxy-17,18,19,10-tetranor-$PGF_{2\alpha}$-IE effectively lowers the intraocular pressure as studied in cats. Thus, substituting carbon 17 in the omega chain with a hetero atom, in this case oxygen, does not render the molecule inactive with respect to the effect on IOP.

It is noteworthy that most of the 17-phenyl,18,19,20-trinor-prostaglandin analogs had poor intraocular pressure lowering effect in cats, even at high doses. It is to be observed that the doses at which compounds were used presented in Table III are lower than those e.g. in Table V. Doses presented in Table III should be explicitly compared with those of the naturally occuring prostaglandins in the same table. The same is true for Table IV. It is clear that with increasing dose side effects may increase. However, the doses of prostaglandin derivatives used in monkeys are comparatively similar to those used in human volunteers, (Table VI) being practically free of side effects.

The effect of some omega chain modified prostaglandin analogs, more specifically 17-phenyl-18,19,20-trinor-$PGF_{2\alpha}$-IE, 15-dehydro-17-phenyl-18,19,20-trinor-$PGF_{2\alpha}$-IE, 15-(R)-17-phenyl-18,19,20-trinor-$PGF$ $2\alpha$-IE, 13,14-dihydro-17-phenyl-18,19,20-trinor-$PGF_{2\alpha}$-IE, and 18-phenyl-19-20-dinor-$PGF_{2\alpha}$-IE on the intraocular pressure of healthy human volunteers is demonstrated in Table VI. All compounds significantly reduced the intraocular pressure. It is particularly significant in this respect that none of the compounds had any significant irritating effect (ocular discomfort) and that 13,14-dihydro-17-phenyl-18,19,20-trinor-$PGF_{2\alpha}$-IE and 15-dehydro-17-phenyl-18,19,20-trinor-$PGF_{2\alpha}$-IE caused very little if any conjunctival/ episcleral hyperemia in man. Thus, omega chain modified, and ring Substituted prostaglandin analogs seem to be unique in that these compounds reduce IOP without causing significant ocular side effects such as hyperemia and discomfort.

The present invention thus describes a group of compounds exhibiting the unique property of causing insignificant ocular side effects while retaining the intraocular pressure lowering effect. From the foregoing it is evident that the crucial modification of the molecule is a ring structure in the omega chain. Furthermore, substituents in the ring structure and/or in the omega chain may be introduced in certain molecules still exhibiting some side-effects in the eye. Hetero atoms may also be introduced into the ring substituted omega chain. Presently, particularly 17-phenyl-18,19, 20-trinor-PGF$_{2\alpha}$-derivatives seem very promising for therapeutic use in glaucoma. From the scientific literature it is evident that PGE$_2$ and PGA$_2$ or their esters lower IOP in the monkey (see Bito et al, 1989). Clinical studies with PGE$_2$ have also been performed demonstrating IOP-lowering effect in man (Flach and Eliason (1988)). Thus, the analogy with PGF$_{2\alpha}$ and its esters lowering IOP in the primate eye is logic. It is most reasonable to assume that other prostaglandins with modified omega chain exhibit essentially the same properties as PGF$_{2\alpha}$ with modified omega chain, i.e. IOP lowering effect without side effects.

TABLE I

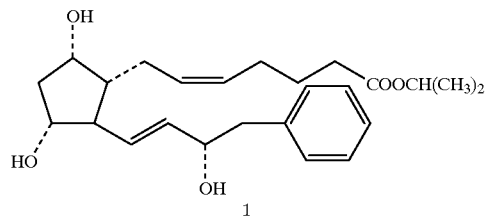
1

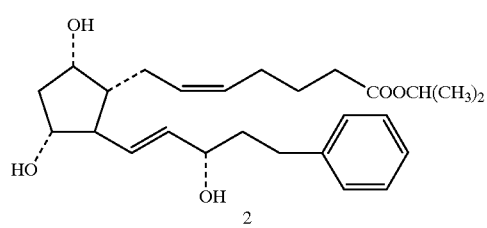
2

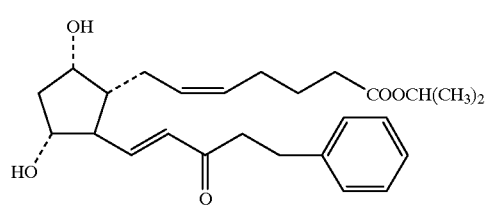
3

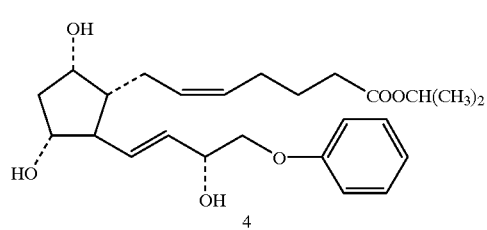
4

TABLE I-continued

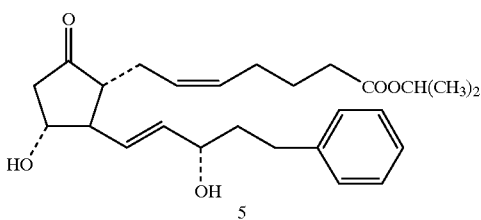
5

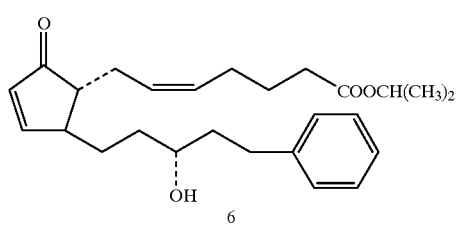
6

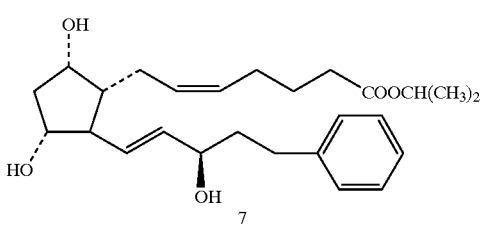
7

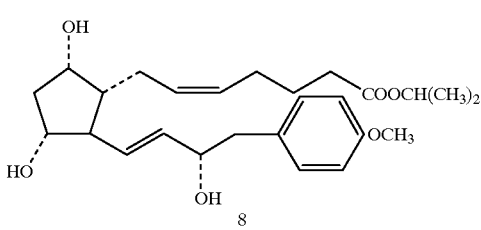
8

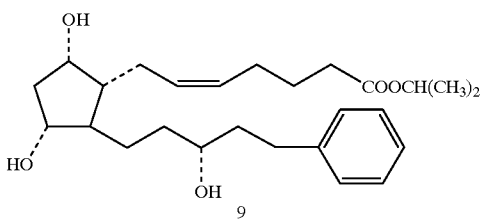
9

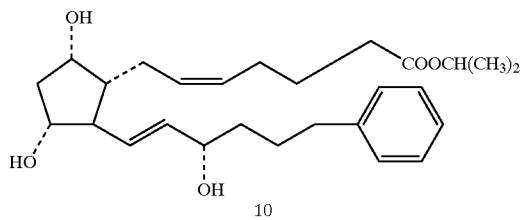
10

TABLE I-continued
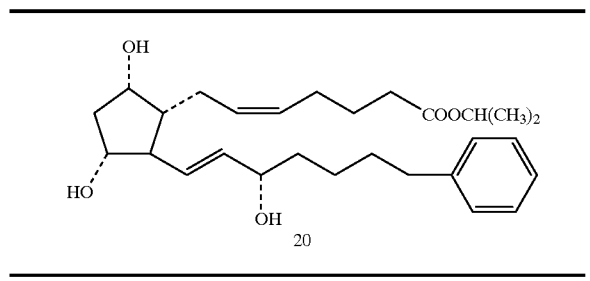
20
TABLE II
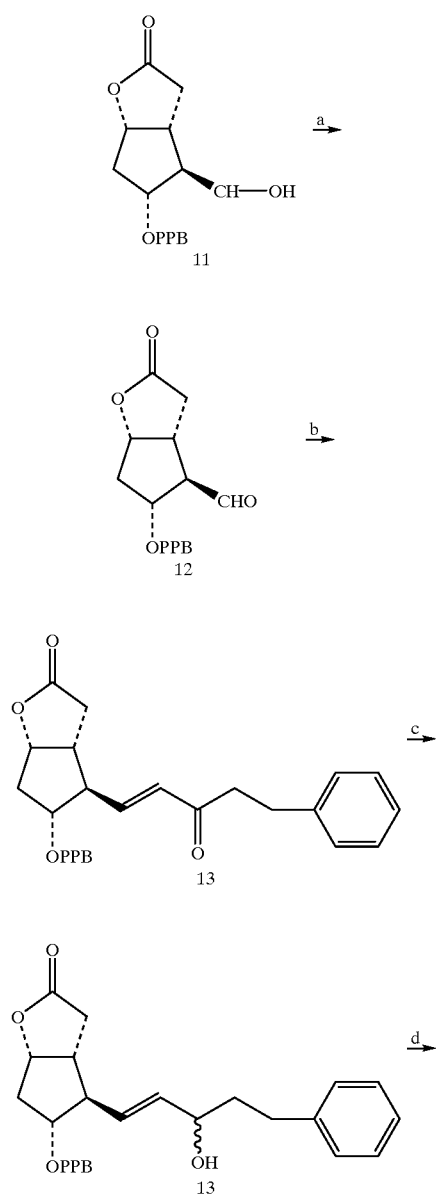
TABLE II-continued
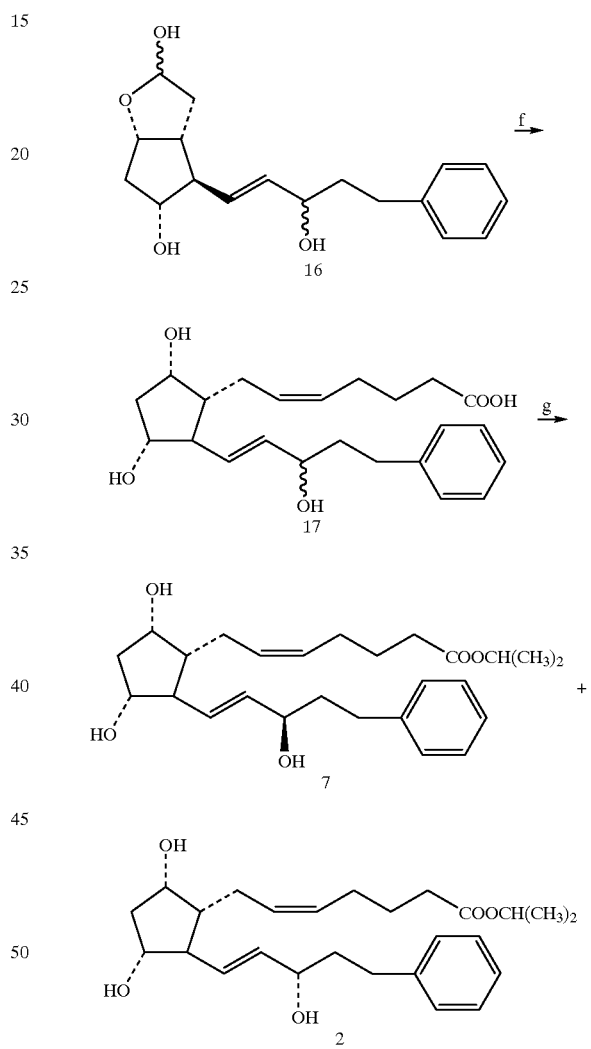
Reagents:
a) DCC/DMSO/DME
b) NaH/dimethyl-2-oxo-4-phenylbutyl phosphonate/DME
c) $CeCl_3 \cdot 7H_2O^-/NaBH_4/CH_3-OH/-78°$ C.$^-$
d) $K_2CO_3/CH_3OH$
e) Dibal/−78° C.
f) $NaCH_2SOCH_3$/(4-carboxybutyl)-triphenylphosphonium bromide/DMSO
g) DBU/iprI/acetone

TABLE III

Irritative effect of naturally occuring prostaglandins ($PGF_{2\alpha}$, $PGD_2$ and $PGE_2$), and omega chain modified analogs applied as isopropylester on the cat eye. The average degree of discomfort was evaluated during 60 min after topical application of the respective test drug. The numbers within parenthesis refer to Table I.

| Substance | | Dose ($\mu$g) | Degree of ocular irritation |
|---|---|---|---|
| $PGF_{2\alpha}$-isoPropylester (-IE) | | 1 | 3.0 ± 0.0 |
| 15-propionate-$PGE_2$-IE | | 0.1–1 | 3.0 ± 0.0 |
| 15-propionate-$PGD_2$-IE | | 1 | 1.3 ± 0.2 |
| 17-phenyl-18,19,20-trinor-$PGF_{2\alpha}$-IE | (2) | 1–5 | 0 |
| 15-dehydro-17-phenyl-18,19,20-trinor-$PGF_{2\alpha}$-IE | (3) | 5 | 0 |
| 15-(R)-17-phenyl-18,19,20-trinor-$PGF_{2\alpha}$-IE | (7) | 1–5 | 0 |
| 13,14-dihydro-17-phenyl-18,19,20-trinor-$PGF_{2\alpha}$-IE | (9) | 1 | 0 |
| 17-phenyl-18,19,20-trinor-$PGE_2$-IE | (5) | 0.3 | 0 |
| 13,14-dihydro-17-phenyl-18,19,20-trinor-$PGA_2$-IE | (6) | 1 | 0 |
| 16-phenyl-17,18,19,20-tetranor-$PGF_{2\alpha}$-IE | (1) | 1 | 2.2 ± 0.3 |
| 16-[4-(methoxy)-phenyl]-17,18,19,20-tetranor-$PGF_{2\alpha}$-IE | (8) | 1 | 0.2 ± 0.1 |
| 18-phenyl-19,20-dinor-$PGF_{2\alpha}$-IE | (10) | 1 | 0.7 ± 0.1 |
| 19-phenyl-20-nor-$PGF_{2\alpha}$-IE | (20) | 1 | 0.5 ± 0.1 |
| 16-phenoxy-17,18,19,20-tetranor-$PGF_{2\alpha}$-IE | (4) | 5 | 0.3 ± 0.2 |

TABLE IV

Degree of conjunctival hyperemia in the rabbit eye after application of naturally occuring prostaglandins ($PGF_{2\alpha, \text{ and } PGE2}$), and omega chain modified analogs applied as isopropylesters.

| Substance | | Dose ($\mu$g) | Degree of hyperemia |
|---|---|---|---|
| $PGF_{2\alpha}$-isopropylester (-IE) | | 0.1 | 2.8 ± 0.2 |
| 15-propionate-$PGE_2$-IE | | 0.5 | 2.7 ± 0.3 |
| 16-phenyl-17,18,19,20-tetranor-$PGF_{2\alpha}$-IE | (1) | 0.5 | 1.3 ± 0.9 |
| 17-phenyl-18,19,20-trinor-$PGF_{2\alpha}$-IE | (2) | 0.5 | 2.0 ± 0.3 |
| 15-dehydro-17-phenyl-18,19,20-trinor-$PGF_{2\alpha}$-IE | (3) | 0.5 | 0.7 ± 0.3 |
| 15-(R)-17-phenyl-18,19,20-trinor-$PGF_{2\alpha}$-IE | (7) | 0.5 | 2.0 ± 0.0 |
| 13,14-dihydro-17-phenyl-18,19,20-trinor-$PGF_{2\alpha}$-IE | (9) | 0.5 | 1.3 ± 0.3 |
| 17-phenyl-18,19,20-trinor-$PGE_2$-IE | (5) | 0.5 | 2.7 ± 0.2 |
| 13,14-dihydro-17-phenyl-18,19,20-trinor-$PGA_2$-IE | (6) | 0.5 | 0.3 ± 0.3 |
| 18-phenyl-19,20-dinor-$PGF_{2\alpha}$-IE | (10) | 0.5 | 0.3 ± 0.2 |
| 19-phenyl-20-nor-$PGF_{2\alpha}$-IE | (20) | 0.5 | 0.2 ± 0.2 |
| 16-phenoxy-17,18,19,20-tetranor-$PGF_{2\alpha}$-IE | (4) | 0.5 | 2.3 ± 0.3 |

TABLE V

Intraocular pressure reducing effect of naturally occuring prostaglandin ($PGF_{2\alpha}$) and omega chain modified analogs as determined in cynomolgus monkeys or cats. Unless specified data were obtained in monkeys. The figures within parenthesis refer to formulas givewin Table I.

| | | | | Time after administration (hours) | | | |
|---|---|---|---|---|---|---|---|
| Substance | | Dose ($\mu$g) | | 0 (mmHg) | 1–2 (mmHg) | 3–4 (mmHg) | 6 (mmHg) |
| | | | E | 11.4 ± 0.7 | 8.3 ± 0.5 * | 8.0 ± 0.6 * | 9.3 ± 0.8 |
| $PGF_{2\alpha}$-isopropylester (IE) | | 1.5 | C | 11.0 ± 0.7 | 10.7 ± 0.4 | 10.1 ± 0.4 | 10.6 ± 0.9 |
| 16-phenyl-17,18,19,20- | | 3.2 | E | 12.7 ± 1.1 | 11.8 ± 1.1 | 9.1 ± 0.8 * | 8.4 ± 0.7 * |
| tetranor-$PGF_{60}$-IE | (1) | | C | 12.8 ± 0.5 | 14.0 ± 0.2 | 13.0 ± 0.8 | 11.7 ± 0.8 |
| 17-phenyl-18,19,20- | | 3.2 | E | 12.8 ± 0.6 | 11.9 ± 0.5 | 8.6 ± 0.3 * | 9.5 ± 0.7 |
| trinor-$PGF_{2\alpha}$-IE | (2) | | C | 13.4 ± 0.6 | 11.7 ± 0.6 | 12.4 ± 0.2 | 11.9 ± 0.7 |
| 13,14-dihydro-17-phenyl- | | 10.4 | E | 11.1 ± 0.9 | 8.3 ± 0.6 | 6.9 ± 0.4 * | 7.7 ± 0.8 |
| 18,19,20-trinor-$PGF_{2\alpha}$-IE | (9) | | C | 10.6 ± 0.7 | 8.8 ± 0.9 | 10.3 ± 1.1 | 9.5 ± 1.0 |
| 18-phenyl-19,20-dinor- | | 3.1 | E | 9.7 ± 0.9 | 9.6 ± 1.1 | 9.6 ± 0.7 | 8.8 ± 0.9 * |
| $PGF_{2\alpha}$-IE | (10) | | C | 10.1 ± 1.0 | 9.4 ± 1.2 | 9.8 ± 1.2 | 9.4 ± 0.9 |
| 16-phenoxy-17,18,19,20- | | 5 ** | E | 20.5 ± 1.2 | 25.7 ± 1.2 | 19.2 ± 1.8 | 15.0 ± 1.2 * |
| tetranor-$PGF_{2\alpha}$-IE | (4) | | C | 20.7 ± 1.2 | 22.7 ± 1.1 | 19.5 ± 0.9 | 19.2 ± 0.8 |
| 16-[4-(methoxy)-phenyl]- | | 3.2 | E | 11.2 ± 0.9 | 10.5 ± 1.3 | 9.8 ± 1.4 | 9.2 ± 0.9 * |
| 17,18,19,20-tetranor-$PGF_{2\alpha}$-IE | (8) | | C | 10.4 ± 1.1 | 10.9 ± 1.0 | 11.3 ± 1.4 | 9.2 ± 0.6 |

TABLE V-continued

Intraocular pressure reducing effect of naturally occuring prostaglandin ($PGF_{2\alpha}$) and omega chain modified analogs as determined in cynomolgus monkeys or cats. Unless specified data were obtained in monkeys. The figures within parenthesis refer to formulas givewin Table I.

| Substance | Dose (µg) | | 0 (mmHg) | 1–2 (mmHg) | 3–4 (mmHg) | 6 (mmHg) |
|---|---|---|---|---|---|---|
| | | | \multicolumn{4}{c}{Time after administration (hours)} | | | |
| 19-phenyl-20-nor- | 1 ** | | E 16.9 ± 1.0 | 16.6 ± 0.7 | 15.8 ± 0.8 * | 18.1 ± 1.2 |
| $PGF_{2\alpha}$-IE | (20) | | C 17.1 ± 0.4 | 18.1 ± 0.6 | 18.9 ± 0.6 | 19.2 ± 0.8 |

* Indicates statistical significance p < 0.05. The substances were applied topically.
** Data obtained in cat eyes.

TABLE VI

Intraocular pressure reducing effect of different omega chain modified and ring substituted $PGF_{2\alpha}$-IE analogs in healthy human volunteers. The substance number is given within paranthesis.

| Substance | | Dose (µg) | n | Eye | 0 (mmHg) | 4 (mmHg) | 6 (mmHg) | 8 (mmHg) |
|---|---|---|---|---|---|---|---|---|
| | | | | | \multicolumn{4}{c}{Time after administration (hours)} | | | | |
| 17-phenyl-18,19,20-trinor- | | 1 | 4 | Exp | 11.9 ± 1.7 | 11.0 ± 0.9 * | 10.1 ± 0.7 * | 9.8 ± 0.7 * |
| $PGF_{2\alpha}$-isopropylester (IE) | (2) | | | Contr | 12.7 ± 1.7 | 13.9 ± 0.7 | 13.5 ± 1.2 | 12.5 ± 0.7 |
| 15-(R)-17-phenyl-18,19,20- | | 10 | 3 | Exp | 12.9 ± 0.9 | 11.8 ± 0.6 | 11.0 ± 0.3 | 11.2 ± 1.3 * |
| trinor-$PGF_{2\alpha}$-IE | (7) | | | Contr | 13.2 ± 1.4 | 11.7 ± 0.9 | 13.8 ± 1.0 | 15.1 ± 1.3 |
| 15-dehydro-17-phenyl- | | 10 | 4 | Exp | 17.7 ± 0.6 | 14.6 ± 0.2 * | 13.6 ± 0.7 * | — |
| 18,19,20-trinor-$PGF_{2\alpha}$-IE | (3) | | | Contr | 17.5 ± 0.7 | 16.4 ± 0.5 | 16.3 ± 1.0 | — |
| 13,14-dihydro-17-phenyl- | | 1 | 4 | Exp | 14.2 ± 0.5 | 13.3 ± 1.1 | 12.2 ± 0.4 * | 12.5 ± 0.9 |
| 18,19,20-trinor-$PGF_{2\alpha}$-IE | (9) | | | Contr | 13.5 ± 0.6 | 14.2 ± 1.2 | 15.2 ± 1.0 | 15.1 ± 0.7 |
| 18-phenyl-19,20-dinor- | | 5 | 3 | Exp | 14.4 ± 1.0 | 12.2 ± 1.1 | 12.4 ± 1.2 | 11.9 ± 0.7 * |
| $PGF_{2\alpha}$-IE | (10) | | | Contr | 15.2 ± 0.1 | 13.7 ± 1.2 | 14.4 ± 0.2 | 13.2 ± 0.5 |

* Indicates statistical significance p < 0.05.

REFERENCES

Bill A (1975). Blood circulation and fluid dynamics in the eye. Physiol. Rew. 55: 383–417.

Bito L Z, Draga A, Blanco D J, Camras C B (1983). Long-term maintenance of reduced intraocular pressure by daily or twice daily topical application of prostaglandins to cat or rhesus monkey eyes. Invest Ophthalmol Vis Sci 24:312–319.

Bito L Z, Camras C B, Gum G G and Resul B (1989). The ocular hypotensive effects and side effects of prostaglandins on the eyes of experimental animals. Progress in clinical and biological research, Vol 312. Ed Laszlo Z Bito and Johan Stjernschantz; Alan R Liss, Inc., New York.

Camras C B, Bito L Z (1981). Reduction of intraocular pressure in normal and glaucomatous primate (Aotus trivirgatus) eyes by topically applied prostaglandin $F_{2\alpha}$. Curr Eye Res 1:205–209.

Camras C B, Podos S M, Rosenthal J S, Lee P Y, Severin C H (1987a). Multiple dosing of prostaglandin $F_2$ $_\alpha$ or epinephrine on cynomolgus monkey eyes. I. Aqueous humor dynamics. Invest Ophthalmol Vis Sci 28:463–469.

Camras C B, Bhuyan K C, Podos S M, Bhuyan D K Master R W P (1987b). Multiple dosing of prostaglandin $F_{2\alpha}$ or epinephrine on cynomolgus monkey eyes. II. Slitlamp biomicroscopy, aqueous humor analysis, and fluorescein angiography. Invest Ophthalmol. Vis Sci 28:921–926.

Camras C B, Siebold E C, Lustgarten J S, Serle J B, Frisch S C, Podos S M, Bito L Z (1988). Reduction of IOP by prostaglandin $F_{2\alpha}$-1-isopropyl ester topically applied in glaucoma patients. Ophthalmology 95 (Suppl): 129.

Crawford K, Kaufman P L, and True Gabel, B'A (1987). Pilocarpine antagonizes $PGF_{2\alpha}$-induced ocular hyptension: Evidence for enhancement of uveoscleral outflow by $PGF_{2\alpha}$. Invest. Ophthalmol. Vis Sci p. 11.

Flach A J, Eliason J A (1988). Topical prostaglandin $E_2$ effects on normal human intraocular pressure. J Ocu Pharmacol 4:13–18.

Giuffrè G (1985). The effects of prostaglandin $F_{2\alpha}$ in the human eye. Graefes Arch Clin Exp Ophthalmol 222: 139–141.

Kaufman P L (1986). Effects on intracamerally infused prostaglandins on outflow facility in cynomolgus monkey eyes with intact or retrodisplaced ciliary muscle. Exp Eye Res 43:819–827.

Kerstetter J R, Brubaker R F, Wilson S E, Kullerstrand L J (1988). Prostaglandin $F_{2\alpha}$-1-isopropylester lowers intraocular pressure without decreasing aqueous humor flow. Am J Ophthalmol 105:30–34.

Lee P-Y, Shao H, Xu L, Qu C-K (1988). The effect of prostaglandin $F_{2\alpha}$ on intraocular pressure in normotensive human subjects. Invest Ophthalmol Vis Sci 29:1474–1477.

Miller W L et al (1975). Biological Activities of 17-Phenyl-18,19,20-Trinor Prostaglandins. 9 p. 9–18.

Nilsson S F E, Stjernschantz J and Bill A (1987). $PGF_{2\alpha}$ increases uveoscleral outflow. Invest. Ophthalmol. Vis Sci Suppl p. 284.

Villumsen J, Alm A (1989). Prostaglandin $F_{2\alpha}$-isopropylester eye drops. Effects in normal human eyes. Br J Ophthalmol 73:419–426.

We claim:

1. A therapeutic composition for topical treatment of ocular hypertension containing a prostaglandin PGF in an amount sufficient to reduce intraocular pressure without causing substantial intraocular irritation, and an ophthamologically compatible vehicle, wherein said prostaglandin is 16-phenoxy, 17, 18, 19-trinorprostaglandin $F_{2\alpha}$.

* * * * *

UNITED STATES PATENT AND TRADEMARK OFFICE
CERTIFICATE OF CORRECTION

PATENT NO. : 6,030,999
DATED : February 29, 2000
INVENTOR(S) : J. Stjernschantz et al.

Page 1 of 1

It is certified that error appears in the above-identified patent and that said Letters Patent is hereby corrected as shown below:

Title page,
Item [30], Foreign Application Priority Data, should be inserted to read:
-- Sep. 6, 1998    [SE]    Sweden         8803110
   Oct. 28, 1988   [SE]    Sweden         8803855
   Sep. 6, 1989    [WO]    WIPO           PCT/SE89/00475 --.

Claim 1,
Line 6, change "16-phenoxy, 17, 18, 19-trinorprostaglandin" to read -- 16-phenoxy, 17, 18, 19, 20-tetranorprostaglandin --

Signed and Sealed this

Eleventh Day of December, 2001

Attest:

*Nicholas P. Godici*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO.    : 6,030,999                              Page 1 of 1
DATED         : February 29, 2000
INVENTOR(S)   : J. Stjernschantz et al.

It is certified that error appears in the above-identified patent and that said Letters Patent is hereby corrected as shown below:

Title page,
Item [30], Foreign Application Priority Data, should be inserted to read:
-- Sep. 6, 1988        [SE]    Sweden          8803110
Oct. 28, 1988          [SE]    Sweden          8803855
Sep. 6, 1989           [WO]    WIPO            PCT/SE89/00475 --.

Column 22,
Line 6, change "16-phenoxy, 17, 18, 19-trinorprostaglandin" to read -- 16-phenoxy, 17, 18, 19, 10-tetranorprostaglandin --

This certificate supersedes Certificate of Correction issued December 11, 2001.

Signed and Sealed this

Twenty-eighth Day of May, 2002

Attest:

JAMES E. ROGAN
*Attesting Officer*    *Director of the United States Patent and Trademark Office*